E. N. Dickerson,
Steam Boiler Superheater.
No 1,993. Reissued June 13, 1865.
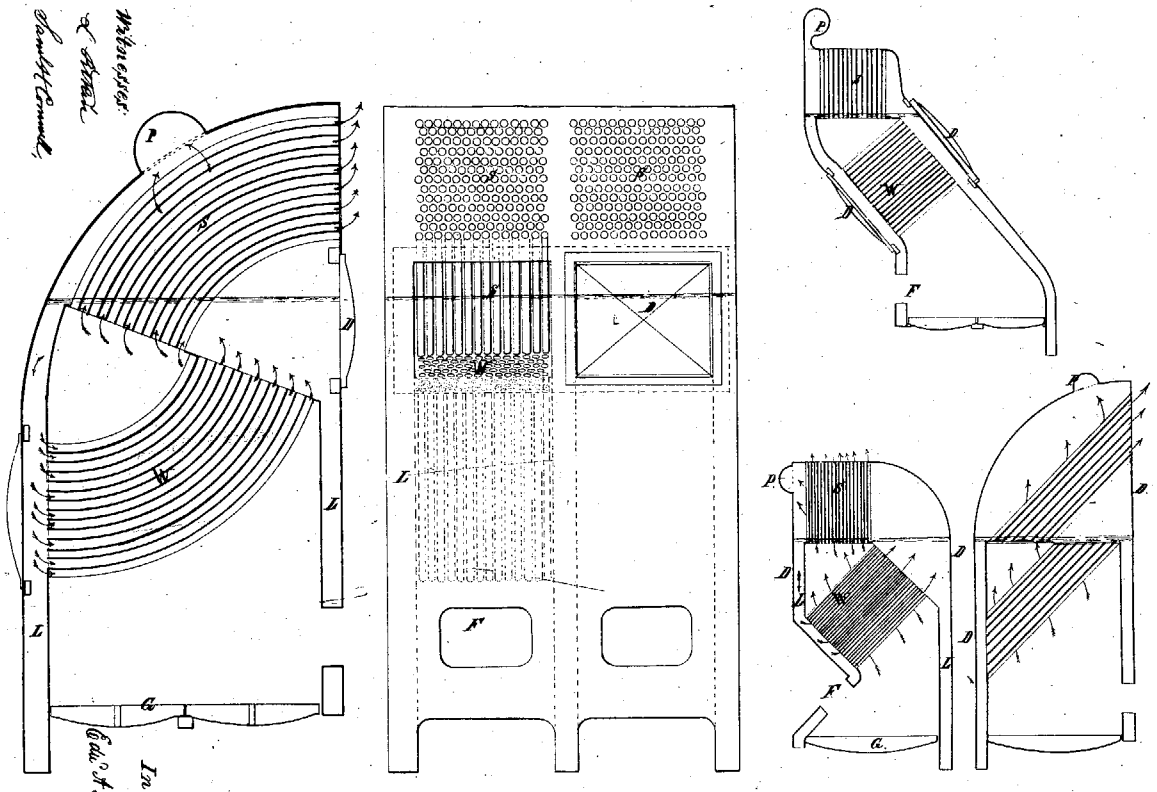
Witnesses:
L. Attach
Saml H. Connell,
Inventor:
Edw. N. Dickerson

UNITED STATES PATENT OFFICE.

EDWARD N. DICKERSON, OF NEW YORK, N. Y.

IMPROVEMENT IN STEAM-BOILERS.

Specification forming part of Letters Patent No. 41,762, dated March 1, 1864; Reissue No. 1,993, dated June 13, 1865.

*To all whom it may concern:*

Be it known that I, EDWARD N. DICKERSON, of the city of New York, in the State of New York, have invented a new and useful Improvement in Steam-Boilers; and I declare the following to be a full and sufficient description, reference being had to the accompanying drawings.

Up to the time of my invention, so far as I know or believe, there has never been made a seperheating-boiler composed of an apparatus for generating the steam and an apparatus for superheating the steam generated, so arranged that through the products of combustion ascending directly from the fire the water to be evaporated should first pass transversely to the hot current in divided streams within tubes or other channels, and then the steam generated in those tubes should repass through the same ascending heated current in divided streams, in some sort of a superheating apparatus, in its passage to the outlet in an opposite direction to that in which the water passed through the evaporating apparatus, whereby it might be dried and rendered effective as pure steam. The advantages of such a boiler are very great. The fire strikes with its greatest energy upon the tubes which contain the water at right angles, or nearly so, to the current of water induced by the heat, and its intensity is divided over the whole length of the tubes, and as a consequence the greatest amount of heat is absorbed, while at the same time the returning current of steam passes again in divided streams in a superheater at right angles, or nearly so, to the heated gases, which have lost their highest temperature, and by its rapid circulation robs the gases of much of their remaining heat, without stagnating and remaining in the boiler in a highly superheated state, as steam does in an ordinary steam-chimney, to its great damage; and as the fire is ascending directly from the grates there is the least impediment to the draft, the most active combustion, and the most extended action of the fire, because the flame is nearly vertical, while the whole boiler stands in the smallest possible compass.

The accompanying drawings show the best arrangements of the boiler to produce the proposed results which have occurred to me, and I believe them to be the best for these reasons: The water is passed through the hot gases in round tubes, which divide it into small streams and present the greatest surface to the impact of the heat, while at the same time they are of the strongest form in which a given thickness of metal can be arranged to contain a bursting force, yet it is obvious that the shape of the channels might be changed to some other than round, and yet embody this element of my invention so long as the water is passed across the ascending current of hot gases in constant circulation and divided currents toward the entrance end of the superheater—as, for example, the shape of the evaporators might be that of the flues in what is known as "Lamb & Sumner's boiler,"—containing water within, and permitting the fire to pass up between them to the superheaters; and the superheater here shown is the best, because experience proves that when the fire passes through a vertical tube and the steam is outside, the destructive effects of the heat are reduced to a minimum, from the fact that the heat does not impinge on the surfaces, but is reflected from them, and also because the lower ends of the tubes are in water; yet it is obvious that any other of the well-known forms of superheaters might be substituted without changing the character of the boiler, so long as the steam is returned again in divided streams in a reverse direction across the same current of heat through which the water had already passed in being converted into steam; and it is obvious that the steam may be made to pass and repass across the current of hot gases in the superheater by the use of diaphragms or partitions, according to the form of the superheater, in ways well known, and yet operate in the entire combination comprising the boiler, just as the best form operates.

The boiler, as a whole, consists of several elements, of which the most important is that the evaporating apparatus should be so arranged, in respect to the superheating apparatus, that while one is above the other in the ascending column of hot gases, yet the generated steam shall be compelled to discharge itself from the evaporators in such manner that it will enter the superheating apparatus and pass through it on its way to the steam-pipe.

This I accomplish by inclining the direction of the current of water through the evaporating apparatus upward toward the entrance of the superheating-apparatus, so that the water and steam, when they emerge from the evaporating apparatus, shall be nearer to the entrance of the superheating apparatus. The effect is that the current of water must set toward the entrance end of the superheating apparatus, and the steam delivered with that current be compelled to pass through the superheating apparatus.

It is found in water tubular boilers that the effect of the rapid generation of steam in the tubes is to cause jets of water to be thrown out of the delivery ends of the tubes, and if these jets are permitted to enter the steam space they are liable to be swept out of the boiler along with the steam. In my boiler, having straight tubes, that evil is controlled by presenting a plate (which in this case is also a door and movable, but which might be fixed) to the delivery ends of the tubes at such an angle to the line of the tubes as to reflect the jets of water and compel them to merge in a solid column of ascent, whereby the speed of the water in the tubes is greatly diminished in the column, and the water is not thrown in such quantities into the steam-room, and the superheater is not overloaded by water which it might not be able to evaporate.

In other forms of water tubular boilers one of the difficulties has been to disperse the products of combustion equally over the water-tubes. In the vertical tubular boiler the upper ends are hottest and the lower ends neglected, and in the curved tubular boiler the current is drawn to some aperture beyond the tubes, and of course acts upon but a small part of the length of the tubes. In my boiler, however, the products of combustion, after passing the evaporating apparatus, are delivered to the chimney through holes in a perforated plate which covers the upper end of the furnace, and consequently the heat of the fire is dispersed over the entire length of the tubes, instead of being confined to a narrow belt across them, while at the same time the intensity of the heat is diminished when it comes to act upon the superheating-surface. It is obvious that these passages from the upper end of the furnace to the chimney might be of different shapes and produce the same effect of dispersion on the evaporator and superheater and be within my invention; but, for obvious reasons, round tubes through a perforated plate are the best. The novelty consists in dispersing the heat above the evaporating apparatus through divided apertures instead of concentrating it through one large opening.

One of the difficulties of boilers generally is that they work great quantities of water with the steam. This effect is due to a variety of causes, mechanical and chemical, one of which is that the steam is drawn out of the boiler from an aperture which opens above a mass of water through which steam is ascending, and which is itself in a state of ebullition, and, as a consequence, the water which the steam brings up with it in finely-divided particles is carried out by the current, and its heat is lost. In my straight tube boiler, however, I draw the steam away from the presence of the water at a place immediately above the descending column of water which is being drawn down to supply the water-tubes, so that the steam is going in an opposite direction from the water, and therefore the usual tendency of the water to rise when the safety-valve is opened is counteracted by the stronger tendency to descend and supply the demand for circulation, and the steam which emerges from the descending column of water, being drawn horizontally across the top of the furnace, has time and space in which to let fall the water which it brings with it out of the evaporator, and this effect would be very useful and decided, even if the superheater was entirely left out of the boiler, since it depends upon a mechanical separation of the steam from the water by mechanical rather than chemical means. It is also desirable, but not necessary, that the superheating apparatus should be so arranged that any water which enters it at the one end may pass out of it at the other end and fall back into the water which is passing into the evaporating apparatus if it has not been evaporated in its passage through the superheater, which is accomplished by making the descending column of water in the front of the boiler open to the end of the superheater, so that the water can run down again into the boiler if it passes through the superheater without being evaporated. It is also of great advantage that both ends of the tubes of water tubular boilers should be accessible without going into the boiler for that purpose and without cutting out a sheet from the boiler. My boiler I arrange so that I reach both ends of the tubes without entering the boiler, simply by taking down a door or plate at each end. These doors may be of any size, so that they permit access as required. In large boilers these doors are a weak surface unless balanced, which, in the straight tubular boiler, may be done by passing a bolt through one or more of the tubes to the opposite side of the boiler, and then securing it on the exterior of the boiler, whereas if the door should be secured to the tube-sheet the effect would be to impose an undue strain upon the tubes.

In the accompanying drawings, Figures 1 and 2 represent a section and front elevation of a boiler with curved tubes; and Figs. 3, 4, and 5 represent straight tubular boilers on the same principle.

The same letters denote similar parts in all.

The size and proportion of these boilers must be left to the judgment of builders, but for ordinary engines four square feet of tubular surface, including the superheater, will be found ample for a horse-power. In stile-boilers the upper tubes need not be more than eighteen inches long. In marine-boilers a greater length is desirable, because of the rolling of the ship.

G G are the grates; L L, the water-legs and spaces; W W, the water-tubes through which the water circulates, and around which the heated gases pass, as shown by the red arrows.

S S are the superheating tubes through which the gases pass after coming from the water-tubes, and around which the steam circulates in divided streams, and by which it is superheated.

P P are the steam-pipes which take off the steam from the boiler, which ought to be continued the whole length of the boiler and entered by perforations, so that the steam may be compelled to come uniformly through the superheater, and not be drawn to a focus, whereby some of the superheating-surface would be out of the line of draft.

D D are steam doors or plates that may be readily removed, so that both ends of the water-tubes will be accessible for repair or cleaning without going into the boiler.

For the purpose of still further utilizing the heat which escapes from the upper end of the superheater, I recommend a hollow chimney, which may be filled in part with water, and where steam may be made, but it is not necessary to show such an apparatus, as any steam-chimney will serve, and it may be connected with the boiler or not, as desired. The upper end of the superheater for each furnace of a series may be closed by a separate damper for each, so that when the fire is being cleaned the draft is not destroyed in the common uptake.

What I claim as my invention, and desire to secure by Letters Patent, is—

1. A superheating steam-boiler, constructed and operating substantially on the principles described.

2. Combining in a boiler an evaporating apparatus so constructed and arranged as to convey the water in divided streams from one water space to another across the column of hot gases ascending from the fire, with a superheating apparatus placed above it, so constructed and arranged as to convey the steam in divided streams across the same column of hot gases in an opposite direction from that in which the water first passed, in order that it may be superheated on its passage to the engine, substantially as described.

3. Specifically, and as the best elements for constructing my new boiler, the arrangement of the tubes in the evaporating apparatus which convey the water in divided streams across the current of hot gases, and other tubes still farther removed from the fire, through which the hot gases pass and around which the stream flows in divided streams, substantially as described.

4. So arranging the steam-delivery aperture leading the steam out from the surface of the water in an inclined straight water tubular boiler, in reference to the descending channel which supplies with water the lower ends of the water-tubes, that the steam shall be drawn out above the descending column of water, so that the tendency of water to rise up to an aperture through which steam is being drawn may be counteracted by the controlling tendency to descent in the sinking column of water, substantially as described, and this whether a superheating apparatus is used or not.

5. The perforated sheet, or other equivalent device, through which the products of combustion are passed from the space above the evaporating apparatus to the chimney, so constructed and arranged that the hot gases will be drawn to the chimney through apertures extending along the length of the evaporating apparatus in divided streams, so as to disperse the heat over the evaporating surface equally, by drawing it equally from the grates, and also to diminish its intensity on the superheating apparatus, substantially as described.

6. In combination with a superheating apparatus inside of a boiler, and forming a part of it, straight water-tubes for evaporating the water, opening at their opposite ends into ascending and descending water-channels, so that the water may ascend in the channel at the higher ends of the tubes and descend in the channel at the lower end, substantially as described.

7. So arranging the evaporating apparatus with reference to the water-level that the highest end shall be under the entrance end of the superheating apparatus, in order to compel the steam to pass through the superheating apparatus, substantially in the manner and for the purposes set forth.

8. Arranging the delivery ends of straight water-tubes so that they shall open against a reflecting-plate, so as to neutralize the tendency of the water to jet out of the tubes and to be forced out of the boiler along with the steam, when in combination with a superheating apparatus which shall receive the steam from the hot water after it has been reflected from the plate, substantially as described.

9. So arranging the superheating apparatus that any water which enters it at its entrance end may drop out of it at its delivery end, and not be carried to the engine, substantially as described.

EDW. N. DICKERSON.

In presence of—
HENRY REDFIELD,
THOMAS C. LAPHAM.